United States Patent [19]

Rose et al.

[11] 4,371,370
[45] Feb. 1, 1983

[54] OXIDATION HAIR DYES COMPRISING BIS-(2,4-DIAMINOPHENOXY)-ALKANOLS AS COUPLING COMPONENTS

[75] Inventors: David Rose, Hilden; Hinrich Möller, Düsseldorf; Norbert Maak, Neuss, all of Fed. Rep. of Germany

[73] Assignee: Henkel Kommanditgesellschaft auf Aktien, Düsseldorf-Holthausen, Fed. Rep. of Germany

[21] Appl. No.: 240,393

[22] Filed: Mar. 4, 1981

[30] Foreign Application Priority Data

Mar. 22, 1980 [DE] Fed. Rep. of Germany ....... 3011191

[51] Int. Cl.$^3$ .......................... A61K 7/13; C07C 93/14
[52] U.S. Cl. ........................................... 8/408; 8/407; 8/409; 8/411; 8/412; 8/416; 564/443; 568/586
[58] Field of Search ................... 8/408, 409, 411, 412; 564/443

[56] References Cited

U.S. PATENT DOCUMENTS 4,171,203  10/1979  Rose et al. ...................... 564/443 X
4,213,758   7/1980  Rose et al. ...............................  8/409
4,259,261   3/1981  Bugaut et al. ................... 564/443 X Primary Examiner—Natalie Trousof
Assistant Examiner—Vera C. Clarke
Attorney, Agent, or Firm—Hammond & Littell, Weissenberger and Muserlian

[57]  ABSTRACT

This invention is directed to bis-(2,4-diaminophenoxy)-alkanols and salts thereof and to compositions of the developer-coupler type for the dyeing of hair, consisting essentially of bis-(2,4-diaminophenoxy)-alkanols or salts thereof as coupling components and, as developer components, the conventional components used in oxidation dyes.

7 Claims, No Drawings

OXIDATION HAIR DYES COMPRISING BIS-(2,4-DIAMINOPHENOXY)-ALKANOLS AS COUPLING COMPONENTS

FIELD OF THE INVENTION

This invention is directed to oxidation hair dyes. More specifically, this invention is directed to bis-(2,4-diaminophenoxy)-alkanols and their use as coupling components in oxidation hair dyes.

BACKGROUND OF THE INVENTION

Dyes known as oxidation dyes, which are produced by oxidative coupling of a developer component with a coupling component, are preferred due to their intense colors and very good fastness. Nitrogen bases such as p-phenylenediamine derivatives, diaminopyridines, 4-aminopyrazolone derivatives, and heterocyclic hydrazones are generally used as developer substances. m-Phenylenediamine-derivatives, phenols, naphthols, resorcinol derivatives, and pyrazolones are useful as coupling components.

Good oxidation dyestuff components must meet the following requirements:

They must produce the desired color nuances in sufficient intensity during oxidative coupling with the respective developer or coupling component. Also, they must possess a capacity for being absorbed by human hair, which capacity ranges from sufficient to very good; and, in addition, they should be toxicologically and dermatologically safe. The production of the strongest possible color shades closely corresponding to the natural hair color nuances is also important. Further, the general stability of the dyestuff produced as well as their fastness to light and to washing and their thermostability, have very special significance for the prevention of color shifts from the original color nuance or even a change in color to difference shades.

Thus, the search for suitable oxidation hair dyes includes the task of finding the proper components that meet the above-mentioned prerequisites in an optimal fashion.

OBJECTS OF THE INVENTION

It is an object of the invention to provide novel bis-(2,4-diaminophenoxy)-alkanols.

It is also an object of the invention to provide agents for the oxidative dyeing of hair that are based upon bis-(2,4-diaminophenoxy)-alkanols as coupling components.

It is a further object of the invention to provide a process for dyeing hair wherein a novel hair dyestuff is employed.

These and other objects of the invention will become more apparent in the discussion below.

DESCRIPTION OF THE INVENTION

Applicants have found novel hair dyestuffs that satisfy the above-mentioned requirements. The hair dyestuffs are based upon oxidation dyes comprising bis-(2,4-diaminophenoxy)-alkanols of the formula

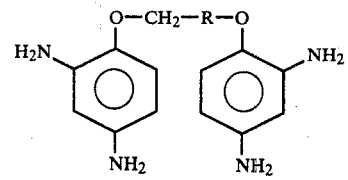

wherein R is selected from the group consisting of the radicals

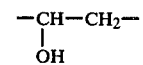

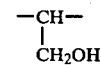

and

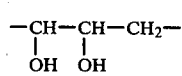

or salts thereof with inorganic or organic acids, as coupling component, and, as developer component, one or more of the conventional developer substances used in oxidation hair dyes. Such hair dyestuffs can meet the above-mentioned requirements to an especially high degree and consequently represent especially valuable combinations in the area of oxidation hair dyes.

The novel compounds of Formula I, which by themselves represent an aspect of the invention, can be prepared by known methods of organic chemistry in several steps. In the first step, 2,4-dinitrophenol is reacted with the respective dibromoalkanol to form bis-(2,4-dinitrophenoxy)-alkanol. This compound is then converted in a second step into the desired bis-(2,4-diaminophenoxy)-alkanol by catalytic hydrogenation. The reaction scheme, wherein R has the above meaning, is as follows:

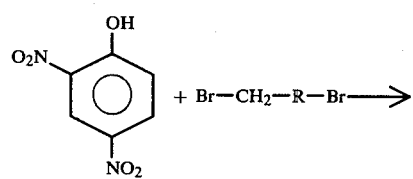

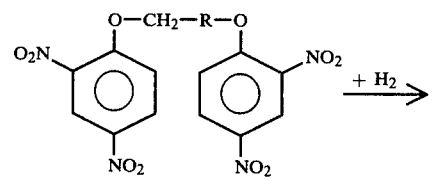

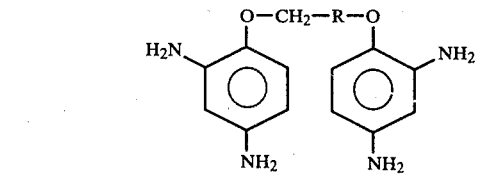

Additional aspects of the invention comprise the use of the bis-(2,4-diaminophenoxy)-alkanols of Formula I as such, or in the form of their salts with inorganic or organic acids, as coupling components in oxidation hair dyes as well as hair dyes that contain the bis-(2,4-diaminophenoxy)-alkanols of Formula I or their salts.

Upon the use of the compounds according to the invention, that is, the bis-(2,4-diaminophenoxy)-alkanols of Formula I and the acid salts thereof, as coupling components together with developers generally used for oxidation hair dyes, the resulting hair dyes yield very intense shades ranging from red brown to black blue, and thus such use represents a considerable expansion of the possibilities in oxidation hair dyeing. In addition, the compounds according to the invention are characterized by very good fastness characteristics of the resulting colors, good solubility in water, good shelf-life, and toxicological as well as dermatological safety.

The bis-(2,4-diaminophenoxy)-alkanols to be used as coupling components according to the invention can be used as such or in the form of their salts with inorganic or organic acids. Useful salts include, for example, chlorides, sulfates, phosphates, acetates, propionates, lactates, citrates, and the like.

Coupling components useful according to the invention include, for example, 1,3-bis-(2',4'-diaminophenoxy)-2-propanol, 1-hydroxymethyl-1,2-bis-(2',4'-diaminophenoxy)-ethane, and 1,4-bis-(2',4'-diaminophenoxy)-butan-2,3-diol, as well as the salts thereof with inorganic or organic acids.

The developer components to be used according to the invention are those that are conventionally used in oxidatively coupled dyestuffs. Examples of such developer components include primary aromatic amines with an additional functional group in the p-position, such as p-phenylenediamine, p-toluenediamine, p-aminophenol, N-methyl-p-phenylenediamine, N,N-dimethyl-p-phenylenediamine, N,N-diethyl-2-methyl-p-phenylenediamine, N-ethyl-N-hydroxyethyl-p-phenylenediamine, chloro-p-phenylenediamine, N,N-bis-hydroxyethylamino-p-phenylenediamine, methoxy-p-phenylenediamine, 2,6-dichloro-p-phenylenediamine, 2-chloro-6-bromo-p-phenylenediamine, 2-chloro-6-methyl-p-phenylenediamine, and 6-methoxy-3-methyl-p-phenylenediamine, and other compounds of this type which also contain one or more additional functional groups such as hydroxyl groups, amino groups, or —NHR$^1$ or —NR$_2^1$ groups, in which R$^1$ represents an alkyl or a hydroxyalkyl moiety with from 1 to 4 carbon atoms. Diamonopyridine derivatives, heterocyclic hydrazone derivatives such as 1-methyl-pyrrolidon(2)-hydrazone, 4-amino-pyrazolone derivatives such as 4-amino-1-phenyl-3-carbamoylpyrazolone-5, and N-butyl-N-sulfobutyl-p-phenylenediamine are additional examples of useful developer components.

Further developer components that can be used according to the invention include tetraaminopyrimidines of the general formula

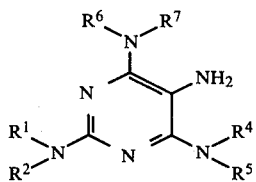

wherein R$^2$ to R$^7$ may each be a hydrogen atom; an alkyl moiety with from 1 to 4 carbon atoms; or the radical —(CH$_2$)$_n$X in which n is an integer of from 1 to 4 and X is selected from the group consisting of a hydroxyl group, a halogen atom, and —NR$^8$R$^9$ in which R$^8$ and R$^9$ are each a hydrogen atom or an alkyl group having from 1 to 4 carbon atoms or together with the nitrogen atoms R$^8$ and R$^9$ form a member selected from the group consisting of a 5 to 6-membered heterocyclic ring optionally containing an additional nitrogen atom or oxygen atom in the ring, as well as their inorganic or organic salts.

The tetraaminopyrimidines to be used as developer components may be used as such or in the form of their salts with inorganic or organic acids, such as, for example, chlorides, sulfates, phosphates, acetates, propionates, lactates, citrates, and the like.

Developer substances suitable for combination with the bis-(2,4-diaminophenoxy)-alkanol coupling components according to the invention also include, for example, the following:

2,4,5,6-tetraaminopyrimidine,
4,5-diamino-2,6-bismethylaminopyrimidine,
2,5-diamino-4,6-bismethylaminopyrimidine,
4,5-diamino-6-butylamino-2-dimethylaminopyrimidine,
2,5-diamino-4-diethylamino-6-methylaminopyrimidine,
4,5-diamino-6-diethylamino-2-dimethylaminopyrimidine,
4,5-diamino-2-diethylamino-6-methylaminopyrimidine,
4,5-diamino-2-dimethylamino-6-ethylaminopyrimidine,
4,5-diamino-2-dimethylamino-6-isopropylaminopyrimidine,
4,5-diamino-2-dimethylamino-6-methylaminopyrimidine,
4,5-diamino-6-dimethylamino-2-methylaminopyrimidine,
4,5-diamino-2-dimethylamino-6-propylaminopyrimidine,
2,4,5-triamino-6-dimethylaminopyrimidine,
4,5,6-triamino-2-dimethylaminopyrimidine,
2,4,5-triamino-6-methylaminopyrimidine,
4,5,6-triamino-2-methylaminopyrimidine,
4,5-diamino-2-dimethylamino-6-piperidinopyrimidine,
2,4,5-triamino-6-piperidinopyrimidine,
2,4,5-triamino-6-anilinopyrimidine,
2,4,5-triamino-6-benzylaminopyrimidine,
2,4,5-triamino-6-benzylidenaminopyrimidine,
4,5-diamino-6-methylamino-2-piperidinopyrimidine,
4,5,6-triamino-2-piperidinopyrimidine,
2,4,6-trismethylamino-5-aminopyrimidine,
2,4,5-triamino-6-di-n-propylaminopyrimidine,
2,4,5-triamino-6-morpholinopyrimidine,
2,5,6-triamino-4-dimethylaminopyrimidine,
4,5,6-triamino-2-morpholinopyrimidine,
2,4,5-triamino-6-β-hydroxyethylaminopyrimidine,
4,5,6-triamino-2-β-amino-ethylaminopyrimidine,
2,5,6-triamino-4-β-methylamino-ethylaminopyrimidine,
2,5-diamino-4,6-bis-γ-diethylamino-propylaminopyrimidine,
4,5-diamino-2-methylamino-6-β-hydroxy-ethylaminopyrimidine,
5-amino-2,4,5-triethylaminopyrimidine, and
2,4-bis-β-hydroxyethylamino-6-anilino-5-aminopyrimidine.

In addition to other color nuances, the coupling components according to the invention also yield dark blue to black blue, especially intense hair colors that are characterized by exceptional light fastness when combined with the respective developer substances. Thus they are also of special importance as nuancing components for the formation of the strongest possible shades that come close to the natural hair color nuances since difficulties frequently are encountered in the production of natural color nuances with the aid of blue coupling components.

In the hair dyestuffs according to the invention, the coupling and developer components generally are used in approximately equimolar amounts. Although the equimolar use proves suitable, it is not disadvantageous to add the coupling component in a certain excess or deficiency. For example, the coupling and developer components can be present in a molar range of from about 2:1 to 1:2, a 10% or less excess or deficiency being preferred.

In addition, it is not necessary that the developer component and the coupling substance are homogeneous or pure products. On the contrary, the developer component may consist of mixtures of the developer compounds to be used according to the invention, and the coupling substance may be in the form of mixtures of bis-(2,4-diaminophenoxy)-alkanols or salts thereof according to the invention. Furthermore, the hair dyestuffs according to the invention may also contain, if desired, conventional, directly applicable dyes in the mixture, provided that such are necessary for the creation of certain color nuances.

The oxidative coupling, that is, the development of the dye, can in principle be carried out with atmospheric oxygen, as is done with other oxidation hair dyestuffs also. However, chemical oxidation agents are advantageously employed. Particularly suitable as such oxidation agents are hydrogen peroxide or its addition compounds with urea, melamine, or sodium borate as well as mixtures of such hydrogen peroxide adducts with potassium peroxydisulfate.

The hair dyes according to the invention are incorporated into respective cosmetic preparations such as creams, emulsions, gels, or also simple solutions for their use and are mixed with one of the mentioned oxidation agents immediately before application to the hair. The concentration of the coupling developer combination in such dyes is from about 0.2 to 5 percent by weight, preferably from about 1 to 3 percent by weight, based on the total weight of the preparation.

For the preparation of creams, emulsions, or gels, the dye components are mixed with the other components normally used in such preparations. Such additional components include, for example, wetting or emulsifying agents of the anionic or nonionic type such as alkylbenzenesulfonates, sulfates of fatty alcohols, higher alkylsulfonates, alkanolamides of fatty acids, adducts of ethylene oxide onto fatty alcohols; thickeners such as methyl cellulose, starch, higher fatty alcohols, paraffin oil, and fatty acids, and perfume oils and hair-conditioning and grooming agents such as pantothenic acid and cholesterol. The mentioned additives are added in the amounts normal for these purposes. For example, wetting and emulsifying agents can be present in concentrations of from about 0.5 to 30 percent by weight, preferably from about 1 to 15 percent by weight, and thickeners can be present in concentrations of from about 0.1 to 25 percent by weight, preferably from about 1 to 15 percent by weight, based, respectively, on the weight of the total preparation.

A hair dye according to the invention can be applied in a weakly acid, neutral or particularly alkaline medium at a pH of 8 to 10, regardless of whether it is in the form of a solution, an emulsion, a cream, or a gel. The application temperatures range from about 15° to 40° C., preferably at room temperature. After the dye is allowed to react for approximately 30 minutes, the preparation is removed by rinsing from the hair to be dyed. The hair is washed with a mild shampoo and dried.

The colors that can be achieved with the hair dyes according to the invention, particularly also the blue shades, produce especially intense color nuances with the use of various developer and coupling components. The colors obtained show good fastness to light, shampooing, and abrasion, and they are easily stripped with reducing agents.

The following examples are intended to illustrate the invention and are not to be constructed as limiting the invention thereto.

EXAMPLES

The bis-(2,4-diaminophenoxy)-alkanols of the invention can be prepared in the following manner:

A.
1,4-BIS-(2',4'-DIAMINOPHENOXY)-BUTAN-2,3-DIOL TETRAHYDROCHLORIDE

First Step: Preparation of 1,4-bis-(2',4'-dinitrophenoxy)-butan-2,3-diol.

A mixture of 19.2 gm (0.1 mol) of 2,4-dinitrophenol (96%), 12.4 gm (0.05 mol) of 1,4-dibromo-butan-2,3-diol, and 6.9 gm (0.05 mol) of potassium carbonate was refluxed for six hours in 20 ml of diethyleneglycoldimethyl ether. After cooling, the product was removed by suction, washed with water, and dried. The intermediate obtained melted at 207°–210° C.

Second Step: 1,4-Bis-(2',4'-diaminophenoxy)-butan-2,3-diol tetrahydrochloride.

An amount of 4.7 gm of the 1,4-bis-(2',4'-dinitrophenoxy)-butan-2,3-diol from the first step was catalytically hydrogenated in 100 ml of ethanol in the presence of 5% palladium on charcoal. After the complete uptake of hydrogen, the catalyst was removed, and the solution was acidified with concentrated hydrochloric acid and evaporated to dryness. The desired compound was obtained in the form of red brown crystals that melted with decomposition at 170° C.

B.
1,3-BIS-(2',4'-DIAMINOPHENOXY)-2-PROPANOL TETRAHYDROCHLORIDE DIHYDRATE

First Step: Preparation of 1,3-bis-(2',4'-dinitrophenoxy)-2-propanol.

A mixture of 19.2 gm (0.1 mol) of 2,4-dinitrophenol (96%), 13.6 gm (0.05 mol) of 1,3-dibromopropanol, and 6.9 gm (0.05 mol) of potassium carbonate was refluxed for six hours in 20 ml of diethyleneglycoldimethyl ether. After cooling, the product was removed by suction, washed with water, and dried. The intermediate obtained melted at 152° C.

Second Step: 1,3-Bis-(2',4'-diaminophenoxy)-2-propanol tetrahydrochloride dihydrate.

This step was carried out analogously to the second step for the preparation of Compound A by catalytic hydrogenation of 1,3-bis-(2',4'-dinitrophenoxy)-2- propanol. The desired compound was obtained in the form of red brown crystals that melted with decomposition at 142° C.

C. 1-HYDROXYMETHYL-1,2-BIS-(2',4'-DIAMINO-PHENOXY)-ETHANE TETRAHYDROCHLORIDE

First Step: Preparation of 1-hydroxymethyl-1,2-bis-(2',4'-dinitrophenoxy)-ethane.

A mixture of 19.2 gm (0.1 mol) of 2,4-dinitrophenol (96%), 13.6 gm (0.05 mol) of 2,3-dibromopropanol, and 6.9 gm (0.05 mol) of potassium carbonate was refluxed for eight hours in 20 ml of dimethylformamide. After cooling, the solution was poured into 1.5 liters of water, and the precipitated product was removed by suction and washed with water. The intermediate obtained melted with decomposition at 129° C.

Second Step: 1-Hydroxymethyl-1,2-bis(2',4'-diaminophenoxy)-ethane tetrahydrochloride.

This step was carried out analogously to the second step for the preparation of Compound A by catalytic hydrogenation of 1-hydroxymethyl-1,2-bis-(2',4'-dinitrophenoxy)-ethane. The desired compound was obtained in the form of brown crystals. IR-spectrum (KBr) cm$^{-1}$: 1630, 1560, 1500, 1400, 1335, 1285, 1230, 1130, 1040, 940, 875, 820.

The above-mentioned bis-(2,4-diaminophenoxy)-alkanols A to C, the preparation of which was described, were used as coupling components below. The following substances were used as developer components:

E-1: p-toluylene diamine
E-2: 2,4,5,6-tetraaminopyrimidine
E-3: p-phenylenediamine
E-4: N,N-dimethyl-p-phenylenediamine
E-5: 2-chloro-p-phenylenediamine
E-6: 2,5-diaminoanisole
E-7: N,N-bis-(β-hydroxyethyl)-amino-p-phenylenediamine
E-8: p-aminophenol
E-9: N-methyl-p-phenylenediamine
E-10: N-ethyl-N-β-hydroxyethyl-p-phenylenediamine
E-11: N-methylamino-4,5,6-triaminopyrimidine.

Procedure

The hair dyes according to the invention were used in the form of a cream emulsion. For this, 0.01 mol of each of the developer substances and coupling substances listed in the table below were worked into an emulsion containing 10 parts by weight of fatty alcohols having 12 to 18 carbon atoms,
10 parts by weight of fatty alcohol sulfate (sodium salt) having 12 to 18 carbon atoms, and
75 parts by weight of water.

Then the pH of the emulsion was adjusted to 9.5 with ammonia, and the emulsion was made up to 100 parts by weight with water. Oxidative coupling was carried out with a 1% hydrogen peroxide solution acting as oxidation agent, 10 parts by weight of the hydrogen peroxide solution being added to 100 parts by weight of the emulsion. The particular dyeing cream, with additional oxidation agent, was applied to human hair which was 90% grey and which had not been especially pretreated, and the cream was left on the hair for 30 minutes. After completion of the dyeing process, the hair was washed out with a conventional shampoo and dried. The colorations obtained by this process are compiled in the table below.

TABLE

| Example | Developer | Coupler | Color Shade Obtained with 1% H$_2$O$_2$ Solution |
|---|---|---|---|
| 1 | E-1 | A | black blue |
| 2 | E-2 | A | dark blue |
| 3 | E-1 | B | black blue |
| 4 | E-2 | B | dark blue |
| 5 | E-1 | C | dark turquoise |
| 6 | E-2 | C | blue grey |
| 7 | E-3 | C | blue grey |
| 8 | E-4 | C | dark blue |
| 9 | E-5 | C | dark violet |
| 10 | E-6 | C | blue grey |
| 11 | E-7 | C | dark blue |
| 12 | E-8 | C | red brown |
| 13 | E-9 | C | blue grey |
| 14 | E-10 | C | blue grey |
| 15 | E-11 | C | dark green |

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

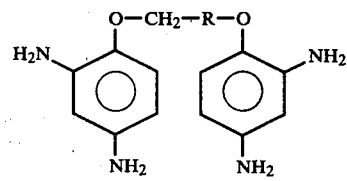

where R is selected from the group consisting of the radicals

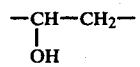

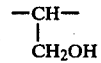

and

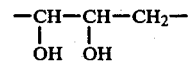

or a salt thereof with an inorganic or organic acid.

2. A composition of the developer-coupler type for the dyeing of the hair, consisting essentially of a carrier, at least one compound of claim 1, as coupling component, and, as developer component, one or more oxidative dye developer components, said coupler and said developer being present in a molar ratio of from about 2:1 to 1:2.

3. The composition of claim 2 which additionally contains conventional additives selected from the group consisting of oxidative dye couplers and direct dyes.

4. The composition of claim 2 wherein the composition comprises from about 0.2 to 5 percent by weight of developer-coupler combination.

5. The composition of claim 4 wherein the composition comprises from about 1 to 3 percent by weight of developer-coupler combination.

6. A process for the dyeing of hair comprising applying to said hair, at temperatures ranging substantially from about 15° to 40° C. for a time sufficient to effect dyeing through atmospheric or chemical oxidation, an effective amount of the developer-coupler composition according to claim 2.

7. The process for the dyeing of hair of claim 6 wherein the oxidation is effected by the action of a chemical oxidation agent.

* * * * *